United States Patent
Matsumoto et al.

(10) Patent No.: US 7,067,523 B2
(45) Date of Patent: Jun. 27, 2006

(54) USE OF PYRONE CARBOXYLATES FOR CONTROLLING PESTS

(75) Inventors: Osamu Matsumoto, Toyonaka (JP); Michihiko Fujinami, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/502,948

(22) PCT Filed: May 21, 2003

(86) PCT No.: PCT/JP03/06308

§ 371 (c)(1),
(2), (4) Date: Jul. 29, 2004

(87) PCT Pub. No.: WO03/099008

PCT Pub. Date: Dec. 4, 2003

(65) Prior Publication Data
US 2005/0159479 A1    Jul. 21, 2005

(30) Foreign Application Priority Data
May 24, 2002  (JP)  ............... 2002-150213
May 24, 2002  (JP)  ............... 2002-150214

(51) Int. Cl.
A01N 46/16   (2006.01)
A61K 31/35   (2006.01)
C07D 309/00  (2006.01)

(52) U.S. Cl. ..................... 514/273; 544/460
(58) Field of Classification Search ................ 424/405; 514/460; 549/273
See application file for complete search history.

(56) References Cited

U.S. PATENT DOCUMENTS 3,122,557 A   2/1964   Molho 6,184,245 B1 *  2/2001  Sugawara et al. .......... 514/444
6,215,016 B1    4/2001  Kawai et al.
6,627,654 B1    9/2003  Kubota et al.
2002/0045657 A1  4/2002  Kubota et al.

FOREIGN PATENT DOCUMENTS

| JP | 51-19126 A | 2/1976 |
| JP | 55-047673 A | 4/1980 |
| JP | 10-16402 A | 1/1998 |
| JP | 2002-363007 A | 12/2002 |

OTHER PUBLICATIONS

O. Hormi et al., "Nucleophilic Vinylic Sybstitution Approach to Derivatives of Fulvic Acid", *Journal of Organic Chemistry*, vol. 52 No. 23, 1987, pp. 5275-5276.
Suzuki et al., "A new and Simple Synthesis of Triacetic Acid Lactone-3-carboxylic Acid (3-Carboxy-4-hydroxy-6-methyl-2-pyrone)", *Synthesis*, 1975, pp. 652-653.

* cited by examiner

*Primary Examiner*—Alton Pryor
(74) *Attorney, Agent, or Firm*—Sughrue Mion, PLLC

(57) ABSTRACT

Pests can be controlled by applying an effective amount of a compound of formula (1):

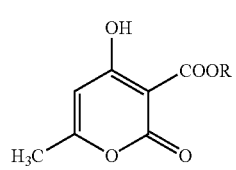

(1)

wherein R is $C_2$–$C_6$ alkyl, $C_3$–$C_6$ cycloalkyl, ($C_3$–$C_6$ cycloalkyl)$C_1$–$C_2$ alkyl, 3,3,3-trifluoropropyl or 3,3,3-trifluoro-2-methylpropyl to pests or habitats of pests.

12 Claims, No Drawings

USE OF PYRONE CARBOXYLATES FOR CONTROLLING PESTS

TECHNICAL FIELD

The present invention relates to use of pyrone carboxylates for controlling pests and a pesticidal use of a pyrone carboxylate for controlling pests.

BACKGROUND ART

In JP-A 51-19126, JP-A-2002-12506 and JP-A-2002-363007, certain pyrone compounds are reported to have activities of controlling pests.

WO97/35565 also describes that certain pyrone carboxylates are useful as active ingredients in pharmaceuticals.

DISCLOSURE OF INVENTION

The present invention provides use of pyrone carboxylates for controlling pests.

Thus, the present invention provides a pesticidal composition comprising as an active ingredient a compound of formula (1):

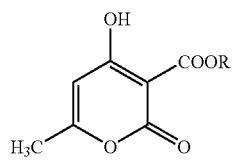

(1)

wherein R is $C_2-C_6$ alkyl, $C_3-C_6$ cycloalkyl, $(C_3-C_6$ cycloalkyl)$C_1-C_2$ alkyl, 3,3,3-trifluoropropyl or 3,3,3-trifluoro-2-methylpropyl; and a method for controlling pests comprising applying an effective amount of the present compound to pests or habitats of pests. The present invention also provides a compound of formula (I) wherein R is $C_3-C_6$ cycloalkyl, $(C_3-C_6$ cycloalkyl)$C_1-C_2$ alkyl, isobutyl or sec-butyl.

In the present invention, the $C_2-C_6$ alkyl represented by R may include, for example, ethyl, propyl, isopropyl, butyl, isobutyl, sec-butyl, pentyl, neopentyl and hexyl. The $C_3-C_6$ cycloalkyl may include, for example, cyclopropyl, cyclobutyl, cyclopentyl and cyclohexyl. The $(C_3-C_6$ cycloalkyl) $C_1-C_2$ alkyl may include, for example, cyclopropylmethyl, 1-cyclopropylethyl, 2-cyclopropylethyl, cyclobutylmethyl, 1-cyclobutylethyl and cyclopentylmethyl. Among those listed above, isobutyl and sec-butyl are preferred in view of efficacies for controlling pests.

The compound of formula (1) can be produced, for example by the following production processes.

(Production Process 1)

Reaction of a malonate of formula (2):

CH$_2$(COOR)$_2$     (2)

wherein R is as defined above with a diketene.

The reaction is carried out in the presence or absence of a solvent, in the presence of a base. The solvent may include, for example, aliphatic hydrocarbons such as hexane, heptane, octane and nonane; aromatic hydrocarbons such as toluene, xylene and mesitylene; halogenated hydrocarbons such as chlorobenzene, dichlorobenzene and benzotrifluoride; ethers such as diisopropyl ether, 1,4-dioxane, tetrahydrofuran and ethylene glycol dimethyl ether; acid amides such as N,N-dimethylformamide; and mixtures thereof.

The base employed in the reaction may include, for example, inorganic bases such as sodium hydroxide, potassium hydroxide, sodium hydride, potassium hydride, sodium carbonate and potassium carbonate; alkaline metal alkoxides such as sodium methoxide, sodium ethoxide and potassium t-butoxide; and tertiary amines such as triethylamine.

The amounts of the reagents used in the reaction are as follows: the malonate of formula (2) is usually used in a ratio of 1 to 10 moles per mole of the diketene, and the base is usually used in a ratio of 1 to 10 moles per mole of the diketene.

The reaction temperature is usually in a range of −5° C. to 100° C., and the reaction time is usually in a range of 1 to 24 hours.

After completion of the reaction, an acidic aqueous solution such as diluted hydrochloric acid can be added to the reaction mixture, and the reaction mixture can be extract with an organic solvent, and then the organic layer obtained can be subjected to ordinary post-treatment procedures such as drying and concentration, to isolate the desired compound of formula (1). The compound of formula (1) thus obtained can be further purified by techniques such as chromatography and re-crystallization.

(Production Process 2)

Reaction of 4-hydroxy-6-methyl-2-oxo-2H-pyrane-3-carboxylic acid of formula (3):

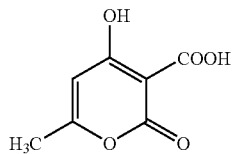

(3)

with an alcohol of formula (4):

ROH     (4)

wherein R is as defined above.

The reaction is usually carried out in a solvent, in the presence of a condensing agent and 4-dimethylaminopyridine. The solvent may include, for example, aliphatic hydrocarbons such as hexane, heptane, octane and nonane; halogenated hydrocarbons such as chlorobenzene, dichlorobenzene and benzotrifluoride; an ethers such as diisopropyl ether, 1,4-dioxane, tetrahydrofuran, ethylene glycol dimethyl ether and diethylene glycol dimethyl ether; and mixtures thereof. The condensing agent may include, for example, dicyclohexylcarbodiimide and 1-ethyl-3-(3-dimethylaminopropyl)carbodiimide hydrochloride (hereinafter abbreviated as WSC). The amounts of the reagents used in the reaction are as follows: per mole of 4-hydroxy-6-methyl-2-oxo-2H-pyrane-3-carboxylic acid represented by formula (3), the alcohol of formula (4) is usually used in a ratio of 1 mole to excess moles, the condensing agent is usually used in a ratio of 1 to 5 moles, and 4-dimethylaminopyridine is usually used in a ratio of 0.01 to 1 mole.

The reaction temperature is usually in a range of −5° C. to 100° C., and the reaction time is usually in a range of 1 to 48 hours.

After completion of the reaction, water can be added to the reaction mixture, and the reaction mixture can be extract with an organic solvent, and then the organic layer obtained can be subjected to ordinary post-treatment procedures such as drying and concentration, to isolate the desired compound of formula (1). The compound of formula (1) thus obtained can be further purified by techniques such as chromatography and re-crystallization.

4-Hydroxy-6-methyl-2-oxo-2H-pyrane-3-carboxylic acid of formula (3) can be produced for example by hydrolyzing an ethyl ester obtained by a reaction of a diketene and sodium diethyl malonate in accordance with the method described in Synthesis, p652 (1975).

Among the compounds of formula (1), the compound in which R is an ethyl group or a propyl group has been described in WO97/35565, and it can be also produced by reacting 4-hydroxy-6-methyl-2-pyrone with a chloroformate ester in accordance with the method described in said publication.

The pests to which the present compound of formula (1) has an activity may include, for example, arthropods such as insects, acarines and isopods.

Specific examples are listed below:
Hemiptera:
Delphacidae such as *Laodelphax striatellus, Nilaparvata lugens* and *Sogatella furcifera;*
Deltocephalidae such as *Nephotettix cincticeps, Nephotettix virescens* and *Recilia dorsalis;*
Aphididae;
Pentatomidae;
Aleyrodidae;
Coccidae;
Tingidae;
Psyllidae;
Leidoptera:
Pyralidae such as *Chilo suppressalis, Cnaphalocrocis medinalis* and *Plodia interpunctella;*
Noctuidae such as *Spodoptera litura, Pseudaletia separata* and *Manestra brassicae;*
Pieridae such as *Pieris rapae;*
Torticoidae such as *Adoxophyes orana;*
Carposimidae;
Lyonetiidae;
Lymantriidae;
Yponomeutidae such as *Plutella xylostella;*
Hesperiidae such as *Parnara guttata;*
Tineidae such as *Tinearia alternata* and *Tineola bisselliella;*
Plusiae;
*Agrotis* spp. such as *Agrotis segetum* and *Agrotis ipsilon;*
*Helicoverpa* spp.;
*Heliothis* spp.;
Diptera:
Calicidae such as *Culex pipiens pallen* and *Culex tritaeniorhynchus;*
*Aedes* spp. such as *Aedes aegypti* and *Aedes albopictus*
*Anopheles* spp. such as *Anopheles sinensis;*
Chironomidae;
Muscidae such as *Musca domesca, Muscina stabulans* and *Fannia canicularis;*
Calliphoridae;
Sarcophagidae;
Anthomyiidae such as *Delia platura* and *Delia antiqua;*
Tephritidae;
Drosophilidae;
Psychodidae;
Simuliidae;
Tabanidae;
Stomoxyidae;
Phoridae;
Caratopogonidae;
Coleoptera:
*Diabrotica* spp. such as *Diabrotica virgifera* and *Diabrotica undecimpunctata howardi;*
Scarabaeidae such as *Anomala cuprea* and *Anomala rufocuprea;*
Cureulionidae such as *Sitophilus zeamais* and *Lissorhoptrus oryzophilus;*
Dermestidae such as *Anthrenus verbasci* and *Attagenus megatoma;*
Tenebrionidae such as *Tenebrio molitor* and *Tribolium castaneum;*
Chrysomelidae such as *Oulema oryzae, Phyllotreta striolata* and *Aulacophora femoralis;*
Anobiidae;
*Epilachna* spp. such as *Epilachna vigintioctopunctata;*
Lyctidae;
Bostrychidae;
Cerambycidae;
Staphylinidae such as *Paederus fuscipes Curtis;*
Dictyoptera:
*Blatella germanica, Periplaneta fuliginosa, Periplaneta americana, Periplaneta brunnea* and *Blatta orientalis;*
Tysanoptera:
Thripidae such as *Thrips palmi, Frankliniella occidentalis* and *Thrips hawaiiensis;*
Hymenoptera:
Formicidae;
Vespidae;
Polistes;
Bethylidae;
Tenthredinidae;
Orthoptera:
Gryllotalpidae;
Acrididae;
Aphaniptera:
*Ctenocephalides canis;*
*Ctenocephalides felis;*
*Pulex irritans;*
Anoplura:
*Pediculus humanus corporis;*
*Pediculus capitis;*
*Pthirus pubis;*
Isoptera:
*Reticulitermes speratus;*
*Coptotermes formosanus;*
Acarinae:
Tetranychidae such as *Tetranychus cinnabarinus, Tetranychus urticae, Tetranychus kanz awai, Panonychus citri* and *Panonychus ulmi;*
Ixodidae such as *Boophilus microplus,* and *Haemaphysalis longicornis;*
Schwiebea such as *Tyrophagus putrescentiae* and *Aleuroglyphus ovatus;*
Epidermoptidae such as *Dermatophgoides fanine* and *Dermatophagoides pteronyssinus;*
Glycyphagidae such as *Glycyphagus privatus, Glycyphagus domesticus* and *Glycyphagus destructor;*
Cheyletidae such as *Cheyletus malaccensis* and *Cheyletus malaccesis;*
Tarsonemidae;
*Chortoglyphus* spp.;
Haplochthoniidae;

Isopoda:

Porcellionidae such as *Porcellionides pruinosus* and *Porcellionides pruinosus*;

Armadillididae such as *Armadillidium vulgare*

The pesticidal composition of the present invention comprises the present compound of formula (1) and an inert carrier such as a solid carrier, a liquid carrier, a gaseous carrier and/or a bait (poison bait base), and optionally adjuvants such as surfactants. The pesticidal composition is formulated into various forms such as an oil solution, an emulsifiable concentrate, a flowable, a water dispersible powder, a granule, a powder, an aerosol, a dust, a fumigant, a poison bait, a microcapsule, spot-on formulation, pour-on formulation, shampoo, sheet, resin, or the like. In each of these formulations, usually the compound of formula (1) is contained in an amount of 0.01% to 95% by weight.

A solid carrier which can be used in the formulation may include, for example, the following materials in fine powder or granular form: clays (e.g. kaolin clay, kieselguhr, synthetic hydrated silicon oxide, bentonite, Fubasami clay and acidic white earth); talc; ceramic; chemical fertilizer (e.g. ammonium sulfate, ammonium phosphate, ammonium nitrate, ammonium chloride and urea); and other inorganic minerals (e.g. sericite, quartz, sulfur, activated carbon, calcium oxide and hydrated silica).

A liquid carrier may include, for example, water; alcohols (e.g. methanol and ethanol); ketones (e.g. acetone and methyl ethyl ketone); aromatic hydrocarbons (toluene, xylene, ethylbenzene and methylnaphthalene); aliphatic hydrocarbons (e.g. hexane, cyclohexane, kerosene and light oil); esters (e.g. ethyl acetate and butyl acetate); nitriles (e.g. acetonitrile and isobutyronitrile); ethers (e.g. diisopropyl ether and 1,4-dioxane); acid amides (e.g. N,N-dimethylformamide and N,N-dimethylacetamide); halogenated hydrocarbons (e.g. dichloromethane, trichloroethane and carbon tetrachloride); organic sulfur compounds (e.g. dimethyl sulfoxide); and vegetable oils (e.g. soybean oil and cotton seed oil).

A gaseous carrier may include, for example, fluorocarbon, butane gas, LPG (liquefied petroleum gas), dimethyl ether and carbon dioxide.

A surfactant may include, for example, alkyl sulfate ester salts; alkylsulfonic acid salts; alkylarylsulfonic acid salt; alkylarylethers and their polyoxyethylene derivatives; polyethylene glycol ethers; polyhydric alcohol esters; and sugar alcohol derivatives.

The other adjuvants may include binders, dispersants and stabilizers, specific examples of which are: casein, gelatin, polysaccharides (e.g. starch, gum arabic, cellulose derivative and alginic acid), lignin derivatives, synthetic water-soluble polymers (e.g. polyvinyl alcohol, polyvinyl pyrrolidone and polyacrylic acid), PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids, and fatty acid esters.

The base materials for poison baits may include, for example, bait ingredients such as grain powders, vegetable oils, sugars and cellulose; antioxidants such as dibutylhydroxytoluene and nordihydroguaiaretinoic acid; preservatives such as dehydroacetic acid; agents for preventing children or pets from erroneously eating such as hot pepper powder; and flavors for attracting pests such as cheese flavor, onion flavor and peanut oil.

When the pesticidal composition of the persent invention is used for controlling pests in agriculture and forestry, the application amount is usually 1 to 10000 g as the amount of the present compound of formula (1) per 10000 $m^2$. Formulations such as emulsifiable concentrates, water dispersible powders or flowable formulations may be usually sprayed after dilution with water to have the compound of formula (1) concentration of 10 to 10000 ppm. Formulations such as granules or powders are usually used as such. These formulations may be applied as such directly to pests, or may be applied to plants such as crops to be protected from pests, or may be used to a soil to control pests inhabiting therein.

When the present pesticidal composition is used for controlling pests, formulations such as emulsifiable concentrates, water dispersible powders or flowable formulations may be sprayed to pests or habitats of pests, after dilution with water to have the compound of formula (1) concentration of 0.01 to 10000 ppm. Formulations such as oils, aerosols, fumigants, or poison baits may be applied as such to pests or habitats of pests. In such case, the amount of the compound of formula (1) applied superficially is usually 10 to 2000 mg per 1 $m^2$ of the treatment area. When applied spatially, the amount to be applied is usually 1 to 1000 mg per 1 $m^3$ of the treatment space.

A method for controlling pests according to the invention is carried out usually by applying an effective amount of the compound of formula (1) as the agent for controlling pests to pest or habitats of pests.

The pesticidal composition of the present invention can also be used in admixture or combination with other insecticides, nematocides, acaricides, bactericides, fungicides, herbicides, plant growth regulators, synergists, fertilizers, soil conditioners, animal feeds, and the like.

Such insecticides, acaricides and/or nematocides which can be used may include, for example, organophosphorus compounds such as Fenitrothion, Phenthion, Diazinon, Chloropyrifos, Acefate, Methidathion, Disulfoton, DDVP, Sulprofos, Cyanophos, Dioxabenzofos, Dimethoate, Phenthoate, Malation, Trichlorfon, Azinphos-methyl, Monocrotophos and Ethion;

Carbamate compounds such as BPMC, Benfuracarb, Propoxur, Carbosulfan, Carbaryl, Methomyl, Ethiofencarb, Aldicarb, Oxamyl and Fenothiocarb;

Pyrethroid compounds such as Ethofenprox, Fenvalerate, Esfenvalerate, Fenpropathrin, Cypermethrin, Permethrin, Cyhalothrin, Deltamethrin, Cycloprothrin, Fluvalinate, Bifenthrin, Tralomethrin, Silafluofen, d-Fenothrin, d-Allethrin, Cyphenothrin, d-Resmethrin, Acrinathrin, Cyfluthrin, Tefluthrin, Transfluthrin, Tetramethrin, Allethrin, Plarethrin, Empenthrin, Imiprothrin and d-Furamethrin;

Thiadiazine derivatives such as Buprofezin; nitroimidazolidine derivatives; nereistoxin derivatives such as Cartap, Thiocyclam and Bensultap; neonicodinoid compounds such as Acetamiprid, Thiamethoxiam and Dinotefuran; chlorinated hydrocarbon compounds such as Endosulfan, γ-BHC and DDT; benzoylphenylurea compounds such as Chlorfluazuron, Teflubenzuron and Flufenoxuron; formamidine derivatives such as Amitraz and Chlordimeform; thiourea derivatives such as Diafenthiuron; phenylpyrazole compounds; methoxadiazon; bromopropylate; Tetradifon; Chinomethionat; Propargite; Fenbutatin oxide; Hexathiazox; Clofentezine; Pyridaben, Fenpyroximate, Tebufenpyrad; polynactin complexes (tetranactin, dinactin, trinactin); Pyrimidifen; Milbemectin; Abamectin; Emamectin; and Azadirachtin (AZAD).

EXAMPLES

The present invention will be further illustrated by the following production examples, formulation examples, and test examples; however, the present invention is not limited to these examples.

First, an example of the production of a compound of formula (1) is described. In the Production Examples, compound numbers correspond to relevant compound numbers in Table 1 shown below.

Production Example 1

8 g of sodium hydride (ca. 60% in oil) was suspended in 200 ml of tetrahydrofuran, and 32 g of diethyl malonate was added dropwise with cooling on ice, and then stirred for 1 hour at room temperature. A solution of 14 g of a diketene in 30 ml of tetrahydrofuran was added dropwise to the reaction mixture with cooling on ice, and then the reaction mixture was stirred for 16 hours at room temperature. Subsequently, 1% hydrochloric acid was poured into the reaction mixture and the reaction mixture was extracted with ethyl acetate. The organic layer was washed with a saturated aqueous solution of sodium chrolide, dried over anhydrous magnesium sulfate, and then concentrated. The residue was subjected to a silica gel column chromatography to obtain 9.5 g of ethyl 4-hydroxy-6-methyl-2-oxo-2H-pyrane-3-carboxylate (Compound No. 1).

$^1$H-NMR (300 MHz, CDCl$_3$/TMS): δ (ppm) 14.00 (s, 1H), 5.95 (s, 1H), 4.44 (q, J=7.1 Hz, 2H), 2.26 (s, 3H), 1.42 (t, J=7.1 Hz, 3H)

Production Example 2

In 30 ml of toluene, 0.85 g of 4-hydroxy-6-methyl-2-oxo-2H-pyrane-3-carboxylic acid, 0.9 g of 1-propanol and 0.12 g of 4-dimethylaminopyridine were dissolved, and 0.96 g of WSC was added to the mixture, and the mixture was stirred at room temperature for 16 hours. Subsequently, water was poured into the reaction mixture, and the reaction mixture was extracted with ethyl acetate. The resultant organic layer was washed with saturated solution of sodium chrolide, dried over anhydrous magnesium sulfate, and concentrated under reduced pressure. The residue was subjected to a silica gel column chromatography to obtain 0.37 g of propyl 4-hydroxy-6-methyl-2-oxo-2H-pyrane-3-carboxylate (Compound No. 2).

$^1$H-NMR (400 MHz, CDCl$_3$/TMS): δ (ppm) 13.98 (s, 1H), 5.94 (s, 1H), 4.33 (t, J=6.7 Hz, 2H), 2.26 (s, 3H), 1.82 (qt, J=7.4, 6.7 Hz, 2H), 1.02 (t, J=7.4 Hz, 3H)

Production Example 3

In a similar manner to the Production Example 2, except for substituting 0.9 g of 2-propanol for 1-propanol, 0.3 g of isopropyl 4-hydroxy-6-methyl-2-oxo-2H-pyrane-3-carboxylate (Compound No. 3) was obtained.

$^1$H-NMR (300 MHz, CDCl$_3$/TMS): δ (ppm) 14.11 (s, 1H), 5.93 (s, 1H), 5.26 (sep, J=6.2 Hz, 1H), 2.54 (s, 3H), 1.41 (d, J=6.2 Hz, 6H)

Production Example 4

In a similar manner to the Production Example 2, except for substituting 1.1 g of 1-butanol for 1-propanol, 0.52 g of butyl 4-hydroxy-6-methyl-2-oxo-2H-pyrane-3-carboxylate (Compound No. 4) was obtained.

$^1$H-NMR (250 MHz, CDCl$_3$/TMS): δ (ppm) 13.99 (s, 1H), 5.94 (s, 1H), 4.37 (t, J=6.6 Hz, 2H), 2.26 (s, 3H), 1.77 (tt J=6.6, 7.2 Hz, 2H), 1.47 (qt, J=7.2, 7.4 Hz, 2H), 0.96 (t, J=7.4 Hz, 3H)

Production Example 5

In a similar manner to the Production Example 2, except for substituting 1.1 g of 2-butanol for 1-propanol, 0.28 g of sec-butyl 4-hydroxy-6-methyl-2-oxo-2H-pyrane-3-carboxylate (Compound No. 5) was obtained.

$^1$H-NMR (400 MHz, CDCl$_3$/TMS): δ (ppm) 14.12 (s, 1H), 5.92 (s, 1H), 5.10 (qt, J=6.0, 6.4 Hz, 1H), 2.25 (s, 3H), 1.86–1.72 (m, 2H), 1.37 (d, J=6.0 Hz, 3H), 0.98 (t, J=7.4 Hz, 3H)

Production Example 6

In a similar manner to the Production Example 2, except for substituting 1.1 g of 2-methyl-1-propanol for 1-propanol, 0.5 g of isobutyl 4-hydroxy-6-methyl-2-oxo-2H-pyrane-3-carboxylate (Compound No. 6) was obtained.

$^1$H-NMR (400 MHz, CDCl$_3$/TMS): δ (ppm) 13.95 (s, 1H), 5.93 (s, 1H), 4.14 (d, J=6.6 Hz, 2H), 2.26 (s, 3H), 2.33–2.11 (m, 1H), 1.02 (d, J=6.8 Hz, 6H)

Production Example 7

In 18 ml of toluene, 0.51 g of 4-hydroxy-6-methyl-2-oxo-2H-pyrane-3-carboxylic acid, 0.67 g of 2-methyl-2-propanol and 0.07 g of 4-dimethylaminopyridine were dissolved, and 0.58 g of WSC was added and the mixture was stirred at room temperature for 16 hours. Subsequently, water was poured into the reaction mixture, and the reaction mixture was extracted with ethyl acetate. The resultant organic layer was washed with a saturated solution of sodium chrolide, dried over anhydrous magnesium sulfate and concentrated under reduced pressure. The residue was subjected to a silica gel column chromatography to obtain 0.22 g of tert-butyl 4-hydroxy-6-methyl-2-oxo-2H-pyrane-3-carboxylate (Compound No. 7).

$^1$H-NMR (400 MHz, CDCl$_3$/TMS): δ (ppm) 14.22 (s, 1H), 5.89 (s, 1H), 2.23 (s, 3H), 1.60 (s, 9H)

Production Example 8

In a similar manner to the Production Example 7, except for substituting 0.79 g of 1-pentanol for 2-methyl-2-propanol, 0.31 g of pentyl 4-hydroxy-6-methyl-2-oxo-2H-pyrane-3-carboxylate (Compound No. 8) was obtained.

$^1$H-NMR (400 MHz, CDCl$_3$/TMS): δ (ppm) 14.00 (s, 1H), 5.94 (s, 1H), 4.36 (t, J=6.8 Hz, 2H), 2.26 (s, 3H), 1.79 (tt, J=6.8, 7.2 Hz, 2H), 1.46–1.30 (m, 4H), 0.92 (t, J=7.2 Hz, 3H)

Production Example 9

In a similar manner to the Production Example 7, except for substituting 0.79 g of 3-methyl-1-butanol for 2-methyl-2-propanol, 0.22 g of 3-methylbutyl 4-hydroxy-6-methyl-2-oxo-2H-pyrane-3-carboxylate (Compound No. 9) was obtained.

$^1$H-NMR (400 MHz, CDCl$_3$/TMS): δ (ppm) 13.98 (s, 1H), 5.94 (s, 1H), 4.40 (t, J=7.0 Hz, 2H), 2.26 (s, 3H), 1.84–1.74 (m, 1H), 1.73–1.65 (m, 2H), 0.96 (d, J=6.4 Hz, 6H)

Production Example 10

In a similar manner to the Production Example 7, except for substituting 0.79 g of 3-methyl-2-butanol for 2-methyl-2-propanol, 0.22 g of 1,2-dimethylpropyl 4-hydroxy-6-methyl-2-oxo-2H-pyrane-3-carboxylate (Compound No. 10) was obtained.

$^1$H-NMR (300 MHz, CDCl$_3$/TMS): δ (ppm) 14.09 (s, 1H), 5.92 (s, 1H), 4.97 (dq, J=6.0, 6.3 Hz, 1H), 2.25 (s, 3H), 1.94 (dqq, J=6.0, 6.4, 6.7 Hz, 1H), 1.32 (d, J=6.3 Hz, 3H), 1.01 (d, J=6.4 Hz, 3H), 0.99 (d, J=6.7 Hz, 3H)

Production Example 11

In a similar manner to the Production Example 7, except for substituting 0.79 g of 3-pentanol for 2-methyl-2-propanol, 0.19 g of 4-hydroxy-6-methyl-2-oxo-2H-pyrane-3-carboxylic acid 1-ethyl-propyl ester (Compound No. 11) was obtained.

$^1$H-NMR (400 MHz, CDCl$_3$/TMS): δ (ppm) 14.11 (s, 1H), 5.92 (s, 1H), 5.05–4.97 (m, 1H), 2.25 (s, 3H), 1.80–1.65 (m, 4H), 0.96 (t, J=7.4 Hz, 6H)

Production Example 12

In a similar manner to the Production Example 7, except for substituting 0.79 g of 2,2-dimethyl-1-propanol for 2-methyl-2-propanol, 0.16 g of 2,2-dimethylpropyl 4-hydroxy-6-methyl-2-oxo-2H-pyrane-3-carboxylate (Compound No. 12) was obtained.

$^1$H-NMR (400 MHz, CDCl$_3$/TMS): δ (ppm) 13.92 (s, 1H), 5.93 (s, 1H), 4.03 (s, 2H), 2.26 (s, 3H), 1.04 (s, 9H)

Production Example 13

In a similar manner to the Production Example 7, except for substituting 0.65 g of cyclopropanemethanol for 2-methyl-2-propanol, 0.12 g of cyclopropylmethyl 4-hydroxy-6-methyl-2-oxo-2H-pyrane-3-carboxylate (Compound No. 13) was obtained.

$^1$H-NMR (400 MHz, CDCl$_3$/TMS): δ (ppm) 14.01 (s, 1H), 5.95 (s, 1H), 4.23 (d, J=7.2 Hz, 2H), 2.27 (s, 3H), 1.38–1.23 (m, 1H), 0.66–0.59 (m, 2H), 0.43–0.37 (m, 2H)

Production Example 14

In 10 ml of toluene, 0.29 g of 4-hydroxy-6-methyl-2-oxo-2H-pyrane-3-carboxylic acid, 0.29 g of α-methylcyclopropanemethanol and 0.04 g of 4-dimethylaminopyridine were dissolved, and 0.32 g of WSC was added to the mixture, and the mixture was stirred at room temperature for 16 hours. Subsequently, water was poured into the reaction mixture, and the reaction mixture was extracted with ethyl acetate. The resultant organic layer was washed with saturated a saturated solution of sodium chrolide, dried over anhydrous magnesium sulfate and concentrated under reduced pressure. The residue was subjected to a silica gel column chromatography to obtain 0.06 g of α-methylcyclopropylmethyl 4-hydroxy-6-methyl-2-oxo-2H-pyrane-3-carboxylate (Compound No. 14).

$^1$H-NMR (396 MHz, CDCl$_3$/TMS): δ (ppm) 14.09 (s, 1H), 5.92 (s, 1H), 3.41 (dq, J=7.9, 6.3 Hz, 1H), 2.25 (s, 3H), 1.46 (d, J=6.3 Hz, 3H), 1.25–1.14 (m, 1H), 0.63–0.52 (m, 2H), 0.57–0.46 (m, 1H), 0.34–0.28 (m, 1H)

Production Example 15

In a similar manner to the Production Example 7, except for substituting 0.78 g of cyclobutylmethanol for 2-methyl-2-propanol, 0.14 g of cyclobutylmethyl 4-hydroxy-6-methyl-2-oxo-2H-pyrane-3-carboxylate (Compound No. 15) was obtained.

$^1$H-NMR (396 MHz, CDCl$_3$/TMS): δ (ppm) 13.96 (s, 1H), 5.93 (s, 1H), 4.34 (d, J=6.7 Hz, 2H), 2.84–2.71 (m, 1H), 2.26 (s, 3H), 2.16–2.01 (m, 2H), 1.99–1.82 (m, 4H)

Production Example 16

In a similar manner to the Production Example 7, except for substituting 1 g of cyclobutanol for 2-methyl-2-propanol, 0.3 g of 4-hydroxy-6-methyl-2-oxo-2H-pyrane-3-carboxylic acid cyclobutyl ester (Compound No. 16) was obtained.

$^1$H-NMR (396 MHz, CDCl$_3$/TMS): δ (ppm) 13.99 (s, 1H), 5.93 (s, 1H), 5.22–5.13 (m, 1H), 2.50–2.39 (m, 2H), 2.38–2.25 (m, 2H), 2.26 (s, 3H), 1.94–1.82 (m, 1H), 1.75–1.61 (m, 1H)

Production Example 17

In a similar manner to the Production Example 7, except for substituting 0.78 g of cyclopentanol for 2-methyl-2-propanol, 0.09 g of 4-hydroxy-6-methyl-2-oxo-2H-pyrane-3-carboxylic acid cyclopentyl ester (Compound No. 17) was obtained.

$^1$H-NMR (400 MHz, CDCl$_3$/TMS): δ (ppm) 14.08 (s, 1H), 5.92 (s, 1H), 5.48–5.35 (m, 1H), 2.26 (s, 3H), 2.05–1.70 (m, 6H), 1.80–1.45 (m, 2H)

Production Example 18

In a similar manner to the Production Example 7, except for substituting 1.03 g of 3,3,3-trifluoropropanol for 2-methyl-2-propanol, 0.41 g of 4-hydroxy-6-methyl-2-oxo-2H-pyrane-3-carboxylic acid 3,3,3-trifluoropropyl ester (Compound No. 18) was obtained.

$^1$H-NMR (400 MHz, CDCl$_3$/TMS) 13.58 (s, 1H), 5.96 (s, 1H), 4.58 (t, J=6.8 Hz, 2H), 2.66 (qt, J=10.4, 6.8 Hz, 2H), 2.28 (s, 3H)

The compounds of formula (1) described in the above production examples are listed together with their compound numbers in the table shown. Compounds represented by formula (1):

TABLE 1

(1)

| Compound Number | R |
|---|---|
| 1 | C$_2$H$_5$ |
| 2 | C$_3$H$_7$ |
| 3 | CH(CH$_3$)$_2$ |
| 4 | C$_4$H$_9$ |
| 5 | CH(CH$_3$)C$_2$H$_5$ |
| 6 | CH$_2$CH(CH$_3$)$_2$ |
| 7 | C(CH$_3$)$_3$ |
| 8 | C$_5$H$_{11}$ |
| 9 | CH$_2$CH$_2$CH(CH$_3$)$_2$ |

TABLE 1-continued

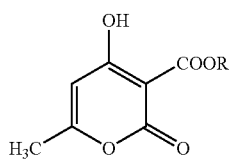

(1)

| Compound Number | R |
|---|---|
| 10 | CH(CH$_3$)CH(CH$_3$)$_2$ |
| 11 | CH(C$_2$H$_5$)$_2$ |
| 12 | CH$_2$C(CH$_3$)$_3$ |
| 13 | CH$_2$(c-C$_3$H$_5$) |
| 14 | CH(CH$_3$)(c-C$_3$H$_5$) |
| 15 | CH$_2$(c-C$_4$H$_7$) |
| 16 | Cyclobutyl |
| 17 | Cyclopentyl |
| 18 | CH$_2$CH$_2$CF$_3$ |

The following will describe some formulation examples wherein parts represent parts by weight.

Formulation Example 1

10 parts of each of the present compounds Nos. 1 to 18, 35 parts of a white carbon containing 50 parts of polyoxyethylene alkyl ether sulfate ammonium salt and 55 parts of water are mixed and pulverized by a wet grinding method to obtain a formulation for each compound.

Formulation Example 2

50 parts of each of the present compounds Nos. 1 to 18, 3 parts of calcium lignosulfonate, 2 parts of sodium lauryl sulfate and 45 parts of a synthetic hydrated silicon oxide are mixed and pulverized thoroughly to obtain a water dispersible powder for each compound.

Formulation Example 3

2 parts of each of the present compounds Nos. 1 to 18, 88 parts of a kaolin clay and 10 parts of a talc are mixed and pulverized thoroughly to obtain a powder formulation for each compound.

Formulation Example 4

20 parts of each of the present compounds Nos. 1 to 18, 14 parts of polyoxyethylene styrylphenyl ether, 6 parts of calcium dodecylbenzenesulfonate and 60 pats of xylene are mixed thoroughly to obtain an emulsifiable concentrate for each compound.

Formulation Example 5

2 parts of each of the present compounds Nos. 1 to 18, 1 part of a synthetic hydrated silicon oxide, 2 parts of calcium lignosulfonate, 30 parts of bentonite and 65 parts of a kaolin clay are mixed and pulverized thoroughly, kneaded thoroughly together with water, and then granulated and dried to obtain a granule formulation for each compound.

Formulation Example 6

20 parts of each of the present compounds Nos. 1 to 18 and 1.5 parts of sorbitan trioleate are mixed with 28.5 parts of an aqueous solution containing 2 parts of polyvinyl alcohol, pulverized (particle diameter of 3μ or less) using a sand grinder, into which 40 parts of an aqueous solution containing 0.05 parts of a xanthane gum and 0.1 parts of aluminum magnesium sulfate is added and 10 parts of propylene glycol is further added, and the mixture is stirred and mixed to obtain a 20% flowable formulation for each compound.

Formulation Example 7

0.1 part of each of the present compounds Nos. 1 to 18 is dissolved in 5 parts of xylene and 5 parts of trichloroethane, and mixed with 89.9 parts of a deodorized kerosene to obtain a 0.1% oil formulation for each compound.

Formulation Example 8

0.1 part of each of the present compounds of the Compound Nos. 1 to 18, 0.2 part of tetramethrin, 10 parts of trichloroethane and 59.7 parts of a deodorized kerosene are mixed and dissolved, and then charged into an aerosol container, which is then fitted with a valve, through which 30 parts of a propellant (liquefied petroleum gas) is charged under pressure to obtain an oily aerosol formulation for each compound.

Formulation Example 9

0.2 part of each of the compounds of the Compound Nos. 1 to 18, 5 parts of xylene, 3.6 parts of a deodorized kerosene and 1 part of an emulsifier [Atomos 300, registered trade name of Atlas Chemical] are mixed and dissolved and charged together with 50 parts of water into an aerosol container, which is then fitted with a valve, through which 40 parts of a propellant (liquefied petroleum gas) is charged under pressure to obtain an aqueous aerosol formulation for each compound.

The following test examples will demonstrate the activity of the present compounds to control pests. In order to clarify the properties of the present pesticidal agents, 4-hydroxy-6-methyl-3-propanoyl-2-pyrone of formula (5):

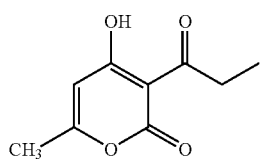

(5)

described in JP-A-51-19126 (hereinafter referred to as the control compound) was used as a control.

Test Example 1

1 μl of a 20 μg/μl acetone solutions of each of the present compounds No. 1 and the control compound was applied onto the surface of the ventral region of the thorax of adult female *Blattela germanica*. These insects were kept with a feed (solid feed for rat, Oriental Yeast, Co., Ltd.) and water for 7 days. Subsequently, the insects were examined for death to obtain mortality (10 insects per group, triplicate). As a result, the present compound No. 1 exhibited 100% mortality death, while the control compound exhibited 30% mortality.

Test Example 2

In a similar manner to the Experiment example 1, using a 20 μg/μl acetone solution of each of the present compounds Nos. 2, 3, 4, 5, 6, 7, 10, 11, 13, 14, 15, 16 and 18 instead of the present compound No. 1 and the control compound, the experiment was carried out to obtain mortality of the cockroach. As a result, each of the present compounds Nos. 2, 3, 4, 5, 6, 7, 10, 11, 13, 14, 15, 16 and 18 exhibited mortality of 80% or higher.

Test Example 3

In a similar manner to the Experiment example 1, using a 2.5 μg/μl acetone solution of each of the present compounds Nos. 5 and 6 instead of the present compound No. 1 and the control compound, the experiment was carried out to obtain mortality of the cockroach. As a result, each of the present compounds of the Compound Nos. 5 and 6 exhibited mortality of 80% or higher, in spite of the low dose of 2.5 μg/μl.

INDUSTRIAL APPLICABILITY

The pesticidal agent of the present invention has an excellent pesticidal activity, and is useful for controlling pests.

The invention claimed is:

1. A method for controlling pests comprising applying an effective amount of a compound of formula (1):

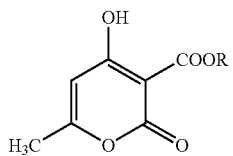
(1)

wherein R is $C_2$–$C_6$ alkyl, $C_3$–$C_6$ cycloalkyl, ($C_3$–$C_6$ cycloalkyl)$C_1$–$C_2$ alkyl, 3,3,3-trifluoropropyl or 3,3,3-trifluoro-2-methylpropyl to pests or habitats of pests.

2. The method according to claim 1 wherein R is $C_2$–$C_6$ alkyl.

3. The method according to claim 1 wherein R is $C_3$–$C_6$ cycloalkyl or ($C_3$–$C_6$ cycloalkyl)$C_1$–$C_2$ alkyl.

4. The method according to claim 1 wherein R is isobutyl or sec-butyl.

5. The method according to claim 1 wherein the pests are arthropods.

6. A method according to claim 1 wherein the pests are insects.

7. A pesticidal composition comprising as an active ingredient a compound of formula (1):

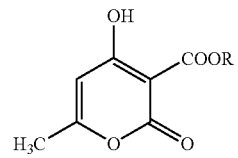
(1)

wherein R is $C_3$–$C_6$ cycloalkyl, ($C_3$–$C_6$ cycloalkyl)$C_1$–$C_2$ alkyl, 3,3,3-trifluoropropyl or 3,3,3-trifluoro-2-methylpropyl and an inert carrier.

8. The pesticidal composition according to claim 7 wherein R is $C_3$–$C_6$ cycloalkyl or ($C_3$–$C_6$ cycloalkyl)$C_1$–$C_2$ alkyl.

9. A compound of formula (1):

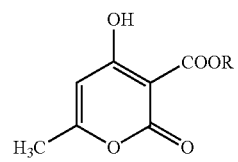
(1)

wherein R is $C_3$–$C_6$ cycloalkyl or ($C_3$–$C_6$ cycloalkyl)$C_1$–$C_2$ alkyl.

10. The compound according to claim 9 wherein R is $C_3$–$C_6$ cycloalkyl.

11. The compound according to claim 9 wherein R is ($C_3$–$C_6$ cycloalkyl)$C_1$–$C_2$ alkyl.

12. A compound of formula (1):

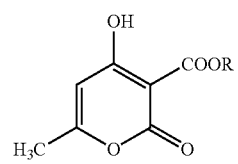
(1)

wherein R is 3,3,3-trifluoropropyl or 3,3,3-trifluoro-2-methylpropyl.

* * * * *